March 20, 1956 W. E. LAMMERTS Plant Pat. 1,463
ROSE PLANT
Filed Feb. 15, 1955
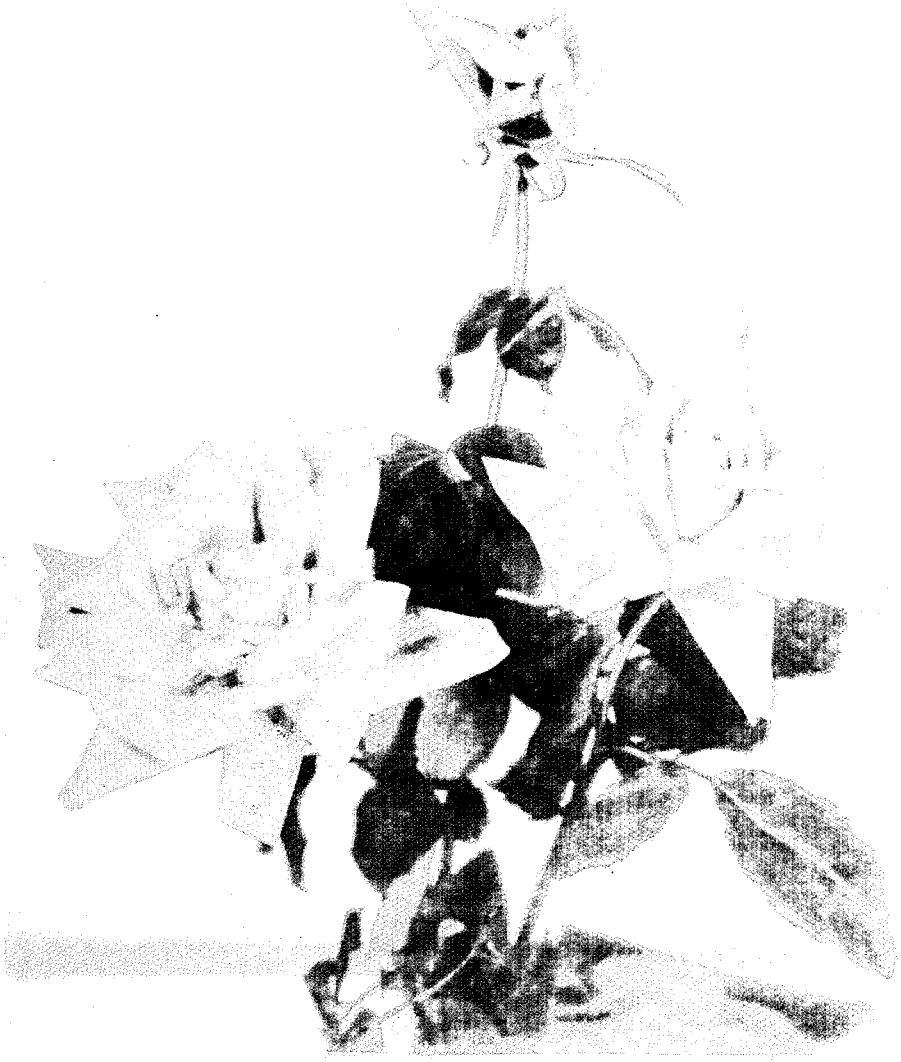
Inventor
W. E. Lammerts
By: Robb & Robb
attorneys.

United States Patent Office

Plant Pat. 1,463
Patented Mar. 20, 1956

1,463

ROSE PLANT

Walter E. Lammerts, Livermore, Calif., assignor to Consolidated Nurseries, Inc., Tyler, Tex., a corporation of Texas Application February 15, 1955, Serial No. 488,447

1 Claim. (Cl. 47—61)

The present invention relates to a new and distinct variety of rose plant of the hybrid tea class, which was originated by me by crossing the variety "Charlotte Armstrong" (Plant Patent No. 455) with the variety "Grand Duchess Charlotte" (Plant Patent No. 774).

As a result of this breeding, I have produced a new rose variety which is endowed with a unique and commercially desirable combination of characteristics of which the following are the most outstanding:

(1) A vigorous and upright growth habit;

(2) Leathery and semi-glossy leaves of medium size and medium Green color, which abundantly clothe the plant;

(3) A distinctive heavy tinge of Garnet Brown color in the young shoots and leaves, which gives a very pleasing appearance to the new growth;

(4) The long urn shape of the buds which are longer than those of the parent variety "Grand Duchess Charlotte" and less pointed than those of "Charlotte Armstrong," said buds having long clasping sepals similar to those of the variety "Soeur Therese" (unpatented);

(5) The abundant production of flowers which are usually borne singly on long cutting stems comparable to those of the variety "Charlotte Armstrong"; and (6) The unusually distinctive color of the buds which are from Chrysanthemum Crimson to Indian Lake in general color tonality, and the equally distinctive color of the newly opened and the mature flowers, said newly opened flowers being from Vermilion to Scarlet in general color tonality, and becoming from Camellia Rose to Sulferino Purple in general color tonality when open for three days, these colors being unlike those of the flowers of either parent variety, as well as distinctly different from the flower color of any other rose of which I am aware.

Asexual reproduction of my new variety by budding, as performed by me at Livermore, California, shows that the foregoing characteristics and distinctions come true to form and are established and transmitted through succeeding propagations.

The accompanying drawing shows typical specimens of the flowers and foliage of my new variety in different stages of development and as depicted in color as nearly true as it is reasonably possible to make the same in a color illustration of this character.

The following is a detailed description of my new variety, with color terminology in accordance with the British Horticultural Color Chart, except where general color terms of ordinary dictionary significance are obvious:

Type: Hardy; tall; bush; outdoor; seedling; for garden decoration.

Class: Hybrid tea.

Breeding: Seedling.

*Seed parent.*—"Charlotte Armstrong."

*Pollen parent.*—"Grand Duchess Charlotte."

Propagation: Holds its distinguishing characteristics through succeeding propagations by budding.

FLOWER

Locality where grown and observed: Livermore, California.

Flowers borne: Usually singly, but occasionally 2 or 3 to the stem; on long stems of normal strength.

Quantity of bloom: Abundant, outdoors.

Continuity: Continuous.

Fragrance: Moderate. Nature—spicy.

Bud:

*Peduncle.*—Long; slender; erect; stiff; almost smooth; with few Green and some Erythrite Red, Plate 0027 prickles. Color—Medium Green and Erythrite Red, Plate 0027.

*Before calyx breaks.*—Size—large. Form—long; pointed; without foliaceous appendages on the surface of the bud; with slender, entire foliaceous parts extending beyond the tip of the bud equal to almost ¼ of its length; with every other sepal (3 of 5) having from 2 to 4 narrow, lance-shaped appendages on the margin, said appendages being about ⅛ to ¼ inch. Color—from Chrysanthemum Crimson, Plate 824/2 to Indian Lake, Plate 826/1.

*As calyx breaks.*—Color—from Currant Red, Plate 821/2 to Cardinal Red, Plate 822/1.

*As first petal opens.*—Size—large. Form—long; from pointed to urn-shape. Color: outside—Canary Yellow, Plate 2 at base, shading through Cherry, Plate 722 to Currant Red, Plate 821/2; inside—Aureolin Yellow, Plate 3 at base, shading through Orient Red, Plate 819/1 to Cherry, Plate 722.

*Opening.*—Opens up well; is retarded from opening by cold weather.

Bloom:

*Size (when fully open).*—Large; from 5 inches to 6 inches.

*Petalage.*—Semi-double (2 or 3 rows); from 22 to 25 petals; arranged regularly.

*Form.*—High-centered at first, but becoming flat open; petals being at first tightly rolled inward, but becoming very loosely rolled outward later at maturity.

Petals:

*Texture.*—Medium thickness; soft; with both inside and outside satiny.

*Shape.*—Outside—obovate; with 1 notch at apex. Intermediate—obovate; with apex often having 2 small notches. Inside—obovate; with apex having 1 small notch.

This description of a newly opened flower was made from a rose grown in a greenhouse in the month of June, at Livermore, California:

Color:

*Outside petal.*—Outside surface—Canary Yellow, Plate 2/2 at base, shading through Begonia, Plate 619 to Cherry, Plate 722/3. Inside surface—Aureolin Yellow, Plate 3/1 at base, shading through Vermilion, Plate 18 to Cherry, Plate 722/3.

*Intermediate petal.*—Outside surface—Canary Yellow, Plate 2 at base, shading through Azalea Pink, Plate 618 to Geranium Lake, Plate 20/2. Inside surface—Aureolin Yellow, Plate 3 at base, shading through Scarlet, Plate 19/1 to Cherry, Plate 722/2.

*Inner petal.*—Outside surface—Canary Yellow, Plate 2 at base, shading through Azalea Pink, Plate 618 to Geranium Lake, Plate 20/2. Inside surface—Aureolin Yellow, Plate 3 at base, shading through Scarlet, Plate 19 to Cherry, Plate 722/2.

This description was made from a rose that was open for 3 days outdoors in the mouth of June, at Livermore, California:

Color:

*Outside petal.*—Outside surface—from Neyron Rose, Plate 623/1 to Sulferino Purple, Plate 26/2. Inside surface—Begonia, Plate 619 at base, shading to Sulferino Purple, Plate 26.

*Inside petal.*—Outside surface—From Begonia, Plate 619/2 to Delft Rose, Plate 020/3. Inside surface—Begonia, Plate 619/1 at base, shading through Camellia Rose, Plate 622/1 to Sulferino Purple, Plate 26/2.

General color effect:

*Newly opened flower.*—From Vermilion, Plate 18/1 to Scarlet, Plate 19/1.

*3-days open.*—From Camellia Rose, Plate 622/1 to Sulferino Purple, Plate 26/1.

Behavior: Drop off cleanly; affected by hot weather by opening quickly and becoming flattened in petal arrangement too soon.

Flower longevity: On bush in garden—3 days in June. Cut roses grown outdoors and kept at livingroom temperatures—4 days in June.

REPRODUCTIVE ORGANS

Stamens: Many; arranged regularly about pistils.

Filaments: Many; most with anthers. Color—Cadmium Orange, Plate 8, tinged with Indian Orange, Plate 713 at base.

Anthers: Medium size; all open at once. Color—Buttercup Yellow, Plate 5/2, tinged with Indian Orange, Plate 713.

Pollen: Abundant. Color—Gold.

Pistils: Many.

Styles: Rather uneven; from short to ¼ inch long; medium caliper; columnar.

Stigma: Color—near Amber Yellow, Plate 505/2.

Ovaries: All enclosed in calyx.

Hips: Ovoid; do not mature. Color (when young)—near Sheel's Green, Plate 860/1.

Sepals: Permanent; very long; spear-shaped; curled.

*Upper surface.*—Pubescent. Color—near Willow Green, Plate 000862/2.

*Under surface.*—Color—near Willow Green, Plate 000862/1.

Seeds: None.

PLANT

Foliage:

*Leaves.*—Compound of 5 to 7 leaflets; medium size; moderately leathery; from dull to semi-glossy.

*Leaflets.*—Shape—oval, with apex mucronate. Base—round. Margin—simply serrate.

*Color.*—Mature: upper surface—near Ivy Green, Plate 0001060/1; under surface—near spinach Green, Plate 0960. Young: upper surface—Green-Bronze; strongly pigmented with anthocyanin. Under surface—strong anthocyanin pigment almost masks basic Willow Green, Plate 000862/2. General effect—Garnet Brown, Plate 00918/3.

*Rachis (the supporting stem of the compound leaf).*—Medium caliper. Upper side—smooth; grooved. Under side—sparsely prickly.

*Stipules.*—Long; narrow; with medium length points turning out at an angle of more than 45°; recurved toward the stem.

*Disease resistance.*—Good resistance to mildew, as determined from comparison with other varieties grown under comparable cultural conditions at Livermore, California.

Growth:

*Habit.*—Tall; bushy; upright; much-branched.

*Growth.*—Free; vigorous.

*Canes.*—Heavy.

*Main stems.*—Color—Dull Green, tinged with Bronze. Thorns—many; long; hooked downward; with long, narrow base. Prickles—few; color—Bronze. Hairs—few; color—Bronze.

*Branches.*—Color—Dull Green, tinged with Bronze. Thorns—many; medium length; hooked downward; with long, narrow base. Prickles—few; color—Reddish. Hairs—few; color—Reddish.

*New shoots.*—Color—Dull Green, strongly tinged with Reddish Bronze, giving generally Garnet Brown, Plate 00918/3 coloration. Thorns—many; medium lengths; hooked downward; with long, narrow base. Prickles—few; color—Reddish. Hairs—few; color—Reddish.

I claim:

A new and distinct variety of rose plant of the hybrid tea class, substantially as herein shown and described, characterized particularly as to novelty by its vigorous and upright habit of growth, its leathery and semi-glossy foliage of medium size which abundantly clothes the plant, the distinctive heavy tinge of Garnet Brown color on the young shoots and foliage, the long urn shape of its buds and their long clasping sepals, its abundant production of flowers which are usually borne singly on long cutting stems, the distinctive and unique general color tonality of the buds from Chrysanthemum Crimson to Indian Lake, and the unusually distinctive general color tonality of the newly opened flowers from Vermilion to Scarlet, later becoming from Camellia Rose to Sulferino Purple in the mature flowers.

No references cited.